(12) United States Patent
Redl et al.

(10) Patent No.: US 7,892,802 B2
(45) Date of Patent: Feb. 22, 2011

(54) FIBRINOGEN-BASED TISSUE ADHESIVE CONTAINING AN ELASTASE INHIBITOR

(75) Inventors: Heinz Redl, Vienna (AT); Guenther Schlag, Vienna (AT); Irmgard Schlag, legal representative, Vienna (AT); Johann Eibl, Vienna (AT)

(73) Assignee: Baxter Aktiengesellschaft (AT)

( * ) Notice: Subject to any disclaimer, the term of this patent is extended or adjusted under 35 U.S.C. 154(b) by 0 days.

(21) Appl. No.: 12/252,988

(22) Filed: Oct. 16, 2008

(65) Prior Publication Data

US 2009/0041748 A1 Feb. 12, 2009

Related U.S. Application Data

(63) Continuation of application No. 11/443,925, filed on May 30, 2006, now Pat. No. 7,459,295, which is a continuation of application No. 09/486,516, filed on Jun. 7, 2000, now Pat. No. 7,091,015.

(51) Int. Cl.
*C12N 9/00* (2006.01)
(52) U.S. Cl. ..................................... 435/183
(58) Field of Classification Search ........................ None
See application file for complete search history.

(56) References Cited

U.S. PATENT DOCUMENTS

| | | |
|---|---|---|
| 4,642,120 A | 2/1987 | Nevo et al. |
| 4,909,251 A | 3/1990 | Seelich |
| 5,084,006 A | 1/1992 | Lew et al. |
| 5,271,939 A | 12/1993 | Robertson et al. |
| 5,397,694 A | 3/1995 | Atkinson et al. |
| 5,418,221 A | 5/1995 | Hammarstrom et al. |
| 5,457,090 A | 10/1995 | Scott et al. |
| 5,631,011 A | 5/1997 | Wadstrom |

FOREIGN PATENT DOCUMENTS

| | | |
|---|---|---|
| AT | 359 652 | 11/1980 |
| AT | 359 653 | 11/1980 |
| AT | 369 990 | 2/1983 |
| AT | 374 367 | 4/1984 |
| DE | 44 34 538 A1 | 4/1995 |
| DE | 240 334 A1 | 12/1995 |
| EP | 0 037 393 B1 | 10/1981 |
| EP | 0 090 997 B1 | 10/1983 |
| EP | 0 131 740 A2 | 1/1985 |
| EP | 0 159 311 A1 | 10/1985 |
| EP | 0 253 198 A1 | 1/1988 |
| EP | 0 315 332 A1 | 5/1988 |
| EP | 0 292 472 B1 | 11/1988 |
| EP | 0 210 160 B2 | 1/1989 |
| EP | 0 519 901 A2 | 12/1992 |
| EP | 0 669 100 A1 | 8/1995 |
| GB | 2 102 811 | 2/1983 |
| WO | WO 92/22309 A1 | 12/1992 |
| WO | WO 94/13329 A1 | 6/1994 |

OTHER PUBLICATIONS

Gobel et al., *Eur. J. Pediatr.*, 129:125-132 (1978).
Henriksson, P. and Nilsson, I.M.; "Effects of leukocytes, plasmin and thrombin ion clotting factors: a comparative in vitro study" *Throm. Res.* 16:301-312 (1979).
International Search Report for PCT/AT98/00202, dated Jan. 25, 1999.
Official Action for A 1449/97 dated Jan. 23, 1998.
Plescia, J et al., "Activation of MAC-1 (CD11b/CD18)-bound factor X by released cathepsin G defines an alternative pathway of leucocyte initiation of coagulation" *Biochem. J.* 319:873-879 (1996).
Simon, D.I. et al., "Fibrin(ogen) is internalized and degraded by activated human monocytoid cells via MAC-1 (CD11b/CD18): A nonplasmin fibrinolytic pathway" *Blood* 82:2414-2422 (1993).

*Primary Examiner*—Michael V Meller
(74) *Attorney, Agent, or Firm*—Morgan, Lewis & Bockius, LLP

(57) ABSTRACT

The present invention provides a fibrinogen-based tissue adhesive which contains an elastase inhibitor.

23 Claims, 4 Drawing Sheets

FIBRINOGEN-BASED TISSUE ADHESIVE CONTAINING AN ELASTASE INHIBITOR

CROSS-REFERENCES TO RELATED APPLICATIONS

This application is a continuation application claiming priority to U.S. application Ser. No. 09/486,516, filed Jun. 7, 2000, which is a U.S. National Phase Application, filed under 35 U.S.C. §371 of Patent Cooperation Treaty Application Number PCT/AT98/00202, filed Aug. 26, 1998, which is claims priority to Austrian Patent Application AT 1449/97, filed Aug. 28, 1997. Each of the aforementioned applications are hereby incorporated by reference in their entirety and for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

The invention relates to a fibrinogen-based tissue adhesive.

Fibrinogen-based tissue adhesives which can also be called fibrin adhesives, in their adhesive action imitate the final phase of blood coagulation. In this instance, fibrinogen is cleaved into fibrin monomers by the action of thrombin which mostly is added to the fibrinogen solution during the glueing procedure, which, however, is also present in every wound. The fibrin monomers agglomerate spontaneously to arranged fiber-type structures called fibrin. This fibrin monomer aggregate then is further stabilized under the action of factor XIIIa by covalent cross linking. At this, in a transamidizing reaction, peptide bonds form between specific glutamine and lysine side chains of the fibrin monomers. The factor XIIIa which likewise is cleaved by thrombin from inactive factor XIII is an active transamidase and, on account of its action, it is also called "fibrin-stabilizing factor".

Although, when applying a tissue adhesive, in principle the same processes occur as in "natural" blood coagulation, in a tissue adhesive the participating components and factors are more concentrated by a multiple than in blood. Due to this, the coagulation of blood also occurs much more rapidly, and the achieved tissue sealing or the formed blood clot are much safer and also more stable.

A prerequisite for the breakthrough of the fibrin adhesives at the end of the 70's was the progress in the fractionation and purification of blood coagulation factors. Because of this it was possible to prepare the natural coagulation factors with such purity and at such a concentration as is required for an efficient tissue adhesion. The first commercially available tissue adhesives were launched on the market at the end of the 70's, and since then they have proven suitable in a large number of possible fields of application; primarily in those fields in which the use of conventional surgical techniques repeatedly have resulted in severe problems, e.g. with severe hemorrhages, when glueing nerves or when inner organs, such as the liver and spleen, were torn.

A further advantage of a fibrin adhesive in contrast to sutures using needle and thread resides in that the tissue or organ to be treated is not additionally damaged by the sewing procedure, and therefore, when using tissue adhesives based on fibrinogen, there are much fewer complications and less obtrusive scars than with conventional surgical sutures. Besides the optimum adhesive effect which comprises a high load bearing capacity and a high inner strength of the sealing as well as a good adherence of the adhesive to the wound or tissue surfaces, respectively, also the processes immediately following adhesion are essential for optimizing tissue adhesives (cf. AT-B-359 652 and 359 653). Among them are the control of the durability of the sealant within the body as well as their capability of being absorbed and the adhesive's properties of enhancing wound healing.

Therefore, for a tissue adhesive not only the rapid and secure sealing effect is of decisive importance but also that the sealant formed or the blood clot formed, respectively, dissolve again in the body within a certain period of time and the wound completely heals up as a consequence of the complete absorption of the formed clot.

In this connection, it is necessary to also control, the (endogenous) process of dissolving the formed blood clot, i.e. the fibrinolysis, by optimizing the tissue adhesive.

In fibrinolysis, the fibrin present in the blood clot formed is degraded and/or removed, and thereby the blood clot is dissolved. At first, under the influence of intrinsic or extrinsic plasminogen activators, such as blood coagulation factors XI and XII, prekallikrein, urokinase or t-PA, the fibrinolytically active plasmin is formed from the inactive plasminogen, said plasmin also cleaving fibrinogen and the blood coagulation factors V and VIII in addition to fibrin.

Since the endogenous fibrinolysis processes mostly start immediately after formation of a clot and thus there is a risk that an existing tissue sealant will not adhere good enough or that a clot formed will become destabilized too early, it has become a rule in tissue glueing to provide for the addition of a plasmin inhibitor or a plasminogen activator inhibitor so as to inhibit the action of plasmin directly or indirectly, to thus protect the sealant, primarily in its initial phase, from a premature fibrinolysis. With the concentration of the inhibitor also a targeted control of the dissolution times (lysis times) of the clot formed or of the sealant, respectively, is possible. The larger the amount of inhibitor provided, the more stable the clot relative to fibrinolysis, i.e., the longer will this clot remain stable and the longer will it take for the adhesive to be completely absorbed.

Thus, when using the fibrinolysis inhibitor, an optimum balance must be found between preventing premature fibrinolysis and an as rapid as possible wound healing process.

In the commercially available tissue adhesives, aprotinin is used as the plasmin inhibitor, which is also called bovine basic pancreatic trypsin inhibitor. Aprotinin is a polyvalent proteinase (kallikrein) inhibitor and inhibits coagulation factors XIIa, XIa, VIIIa as well as, primarily, plasmin and plasmin activators, but also trypsin, chymotrypsin and kallikrein.

Previously, aprotinin has mainly been produced from cattle. Due to the problems involved in the use of bovine material in medicaments which are used for the treatment of humans, however, more and more frequently recombinantly prepared aprotinin is being used.

In tissue sealants, aprotinin is used in an amount of from 20 to 3000 kallikrein inactivator units (KIU)/ml tissue adhesive as a rule, its optimum concentration depending on the fibrinolytic activity of the respective tissue. However, it has been shown that mainly in tissues with high fibrinolytic activity, the fibrinolysis-inhibitory action of aprotinin can be controlled to a very limited extent only, despite the use of high aprotinin concentrations, and thus undesired, early lytic processes may occur.

SUMMARY OF THE INVENTION

Thus, it is an object of the present invention to provide a tissue adhesive with which the disadvantages of the prior art are overcome and with which also primarily with tissue sealants in wounds exhibiting a high plasmin activity, a satisfactory and reliable protection against a premature fibrinolysis will be ensured, wherein the quality of the adhesion must not be negatively affected.

According to the invention, this object is achieved by a fibrinogen-based tissue adhesive which is characterized in that it comprises an admixed elastase inhibitor. For, surprisingly, it has been shown that the fibrinolysis process cannot only be prevented by inhibiting plasmin or by inhibiting the activation of plasminogen to plasmin, but also by elastase inhibitors or by inhibitors whose fibrinolysis-inhibiting action is mainly based on a non-plasmin fibrinolysis mechanism, respectively. For reasons of simplicity, such non-plasminogen fibrinolysis inhibitors are encompassed by the term "elastase inhibitor" for the purposes of the present invention. It has been speculated that besides the plasmin-mediated fibrinolysis, also further fibrinolytic processes might exist which are not based on plasmin (e.g. a lysosomal process; cf. Simon at al., BLOOD 82 (8) (1993), pp. 2414-2422), and which cannot be substantially inhibited by aprotinin; yet, it has also been shown that this non-plasmin fibrinolytic pathway could not be inhibited by specific elastase-inhibiting peptides, such as N-methoxy-succinyl-L-alanyl-L-prolyl-L-valanyl chloromethyl ketone (AAPVCK), either (cf. Simon et al.). It was the more surprising that it could be found out in the course of the present invention that inhibitors which do not have any (substantial) plasminor plasminogen activator-inhibiting activities, i.e. the elastase inhibitors of the invention, can ensure a very well controllable lytic process of the clot formed both in vitro and in vivo. This proved particularly suitable in tissues with increased fibrinolytic activity in which they can prevent early lysis even at moderate concentrations.

Premature lysis also plays a role in tissues with high fibrinolytic activity, primarily within the first time after the sealing has been made, since premature lysis may lead to a (partial) detachment of the sealant and, thus, to rebleeding.

Furthermore, it has been shown that the elastase inhibitor to be used according to the invention in the tissue adhesive exhibited its fibrinolytic activity not only in combination with conventional inhibitors acting on plasmin, but that even the entire fibrinolysis inhibition can be ensured by the elastase inhibitor alone. One particular embodiment of the present invention thus consists in that the tissue adhesive does not contain any further active components besides fibrinogen, the elastase inhibitor, and, optionally, factor XIII.

In the present adhesive, the fibrinogen concentration corresponds to that of known tissue adhesives and, as a rule, should be at least more than 50 mg, in particular more than 70-80 mg of fibrinogen/ml, i.e. at least approximately the 20-fold of the fibrinogen concentration in blood (2-4 mg/ml). Preferably, the fibrinogen is present in a further purified form as compared to the cryoprecipitate.

Preferred elastase inhibitors within the scope of the present invention are selected from the group of eglin, elastase-αhd 1-proteinase inhibitor, $\alpha_1$-antiprotease, elafin, leukocyte protease inhibitor, in particular a leukocyte fraction, preferably a granulocyte-derived fraction, or human secretory leukoprotease inhibitor, or mixtures thereof. As the leukocyte fraction, e.g., a cell lysate, in particular one derived from human cells, may be used. Other elastase—or other fibrinolysis inhibitors which do not act on plasmin may be assayed by the skilled artisan for their usefulness in the tissue adhesive of the invention in a simple manner by means of the assaying systems disclosed in the Examples or by applying the elastase inhibiting assays known from the prior art. The preferred elastase inhibitors include also various derivatives of the elastase inhibitors of the invention, e.g. fragments or forms of these inhibitors which have been modified chemically or by (recombinant) protein design, wherein, however, it is, of course, always necessary that these derivatives have the qualitative elastase-inhibitor property of the basic inhibitor.

Preferably, the tissue adhesive according to the invention is exclusively comprised of human proteins, wherein also recombinantly prepared human proteins are to be understood as being "human proteins". Preferably, therefore, the proteins used in the tissue adhesive are prepared either from blood, plasma, cryoprecipitate, or from a recombinant cell culture.

A particularly preferred tissue adhesive is characterized in that it is exclusively composed from human blood or plasma proteins.

The ratio of the amounts of elastase inhibitor to mg of fibrinogen preferably is from 1:100 to 1:150,000, preferably from 1:500 to 1:110,000. Expressed in units of inhibitor to g of fibrinogen, preferably at least $10^{-6}$ U/g fibrinogen are admixed to the tissue adhesive. Particularly preferred is a range of between $10^{-3}$ and 10 U/g of fibrinogen. The amount of inhibitor admixed in the tissue adhesive of the invention, which inhibitor may also naturally be present in blood or plasma, respectively, preferably is at least 20×, in particular at least 50× higher than its physiological concentration in blood or plasma, respectively. The tissue adhesive of the invention may, e.g., be composed as follows: 75-115 mg/ml clottable protein, 50-110 mg/ml, preferably 70-110 mg/ml, thereof being fibrinogen; optionally 1-50, preferably 10-50, IU factor XIII/ml. As the inhibitor, e.g. eglin may be admixed in an amount of between 1-100 μg/ml or $\alpha_1$-antiprotease at 0.01-1 U/ml. As a rule it will be sufficient to admix the elastase inhibitor in an amount which corresponds to the fibrinolysis-inhibiting activity of aprotinin in known tissue adhesives.

Depending on the purpose of the sealing, the adhesive according to the invention may contain plasminogen or may be free from plasminogen. If plasminogen is contained, it should be contained in an amount of at least 0.0001 mg/mg of fibrinogen, preferably more than 0.001, in particular more than 0.01. With the presence of plasminogen in the tissue adhesive, based on its activation to plasmin, it is also possible to define the fibrinolysis properties of the tissue adhesive even more clearly.

On the other hand, the tissue adhesive, in a further preferred embodiment, does not contain any plasminogen at all or contains only a small amount thereof, respectively.

As has been mentioned, the presence of the elastase inhibitor as the only fibrinolysis inhibitor in a tissue adhesive surprisingly suffices for the functionality of the adhesive according to the invention. Preferably, however, also a plasmin inhibitor or a plasmin activator inhibitor is used besides the elastase inhibitor, which also contributes to a better control of lysis, of absorption, and thus of wound-healing. Preferred plasmin inhibitors or plasminogen activator inhibitors are primarily aprotinin, but also $\alpha_2$-macroglobulin, $\alpha_1$-antitrypsin, ε-amino-caproic acid, tranexamic acid or mixtures of these substances. Although in some instances authors have also ascribed $\alpha_1$-antitrypsin, e.g., certain actions on elastase, the substances mentioned here are viewed as plasmin or plasminogen activators, respectively, since this is the primary activity exhibited by these substances in the present field.

This, of course, also applies for the purposes of the present invention. Moreover, also anti-adhesive additives, e.g. hyaluronic acid, may be contained.

A further preferred embodiment of the tissue adhesive according to the invention consists in providing an antibiotic in the adhesive, as has already been suggested in AT-B-369, 990. Particularly preferred antibiotics are selected from the group of aminoglycosides, betalactams, polypeptides, phosphomycin, tetracyclines or mixtures thereof. In a further preferred embodiment, the antibiotic is present in the form of a poorly soluble-derivative.

Preferably, also factor XIII is provided in the tissue adhesive according to the invention so that the inner strength of the clot and the strength and durability of the adhesion will be positively influenced. To this end, factor XIII is preferably used in an amount of from 1-50 units/ml, preferably around 10 U/ml. Based on fibrinogen, factor XIII is preferably present in a minimum concentration of 0.001 U/mg of fibrinogen, in particular at least 0.1 U/mg of fibrinogen. Depending on the type of adhesion or type of tissue, however, the optimum factor XIII concentration may easily be optimized by any skilled artisan. If an antibiotic is present in the tissue adhesive, it is basically recommendable to provide somewhat more factor XIII (cf. AT-B-369,990).

Preferably, the tissue adhesive according to the invention is free of kininogenic proteins (such as, e.g., kallikrein, etc.), whereby interfering side reactions can be prevented from the beginning.

According to a preferred embodiment, the tissue adhesive according to the invention is present in combination with a solid surface as a fleece, whereby primarily for large-area wounds, an optimum wound closure and an optimum covering will be attained. Examples of such fleeces have been listed in AT-B 374,367. The solid surface of the fleece thus preferably is a collagen, gelatin or polysaccharide surface, wherein, of course, also further medically suitable surfaces which optionally may also have been impregnated for the specific purpose of use may be employed.

It has been shown that according to the invention, with the tissue adhesive comprising an elastase inhibitor a resistance to lysis can be achieved for a period of at least 10 hours, preferably 15 hours, even in an environment with high fibrinolytic activity. Resistance to lysis according to the present invention means that a respective fibrin clot will not be degraded within a certain period of time, i.e. it remains in existence. Determination of the resistance to lysis is, e.g., effected by a photometric measurement in dependence on time. A preferred tissue adhesive according to the present invention thus has a resistance to lysis of at least 10 hours, preferably at least 15 hours, in an environment of high fibrinolytic activity. By "high fibrinolytic activity", e.g., a plasmin activity is understood which is above the physiological plasmin potential. The fibrinolytic potential may, e.g., be expressed by the plasminogen concentration (cf., e.g., Henriksson et al., Thrombosis Research 16: 301-312; 1979). This property of a resistance to lysis may be checked by any skilled artisan by a sample assay, as described in the Examples.

When being applied, the tissue adhesive of the invention preferably is present in solution, yet for storage purposes, either deep freezing of the solution so that the tissue adhesive is present in deep-frozen form, or lyophilizing of the adhesive, i.e. providing it in lyophilized form, is recommendable. By "lyophilized form", of course, only a tissue adhesive preparation made storable by freeze-drying is to be understood which in a subsequent reconstitution thereof can be reconstituted almost completely ( i.e. to at least 80%) within a few minutes at 37° C.

The tissue adhesive according to the invention advantageously is present in virus-inactivated force.

This inactivation treatment preferably is ensured by a tenside and/or heat treatment, e.g. by a heat treatment in the solid state, in particular by a vapour treatment according to EP-0 159 311, or EP-0 519 901 or EP-0 674 531.

Further treatments for inactivation of viruses also comprise a treatment by chemical or chemical/physical methods, e.g. with chaotropic substances according to WO94/13329, DE 44 34 538 or EP 0 131 740 (solvent), or photoinactivation.

Nanofiltration also is a preferred method for depleting viruses within the scope of the present invention.

According to a preferred embodiment, the elastase inhibitors admixed according to the invention may also be of recombinant origin.

Furthermore, the present invention relates to a tissue adhesive system comprising, as one component thereof, a tissue adhesive according to the invention which comprises an elastase inhibitor.

As a rule, the tissue adhesive-system of the invention comprises a thrombin component as a further component, in which thrombin is present either in liquid form or as a lyophilisate capable of being reconstituted, wherein the thrombin component may have different concentrations when used in the adhesion, depending on the field of application.

A tissue adhesive system which also falls within the scope of the present invention is characterized in that it comprises a fibrinogen component and a component separate therefrom which contains an elastase inhibitor. As a rule, however, it is suitable to provide the fibrinolysis inhibitor component in the fibrinogen component (cf. AT-B-359;652 and 359,653). By suitable application devices, the inhibitor component may, however, also be supplied separately from the fibrinogen component. Preferably, that component which contains an elastase inhibitor at the same time also contains thrombin, it again being possible to provide this component either as a lyophilisate or as an (optionally deep-frozen) solution.

The tissue adhesive systems according to the invention further comprise suitable application devices for the system component(s). In particular, double syringe systems as described in EV 0 037 393, EP 0 210 160 or EP 0 292 472, or application devices as described in EP 0 315 322 or EP 0 669 100 have proven suitable. With these special application devices, also those embodiments in which the inhibitor is applied in the thrombin component will yield reliable adhesive results.

The present adhesive is suitable for all the fields of known applications possible for fibrin adhesives. It has, however, proven particularly suitable when providing adhesions in fields with high fibrinolytic activity. Thus, a subject matter of the present invention is also the use of the tissue adhesive of the invention or of a tissue adhesive system of the invention, respectively, for producing a preparation or an application device, respectively, to be used in fields with high fibrinolytic activity, in particular in urology. A subject matter of the present invention is, moreover, a method for using a tissue adhesive of the invention or a tissue adhesive system of the invention, respectively, in surgery in fields involving high fibrinolytic activity, in particular in urology.

BRIEF DESCRIPTION OF THE DRAWINGS

The invention will now be explained in more detail by way of the following Examples and drawing figures, to which, however, it shall not be restricted.

DETAILED DESCRIPTION OF THE INVENTION

Examples

Figure 1:
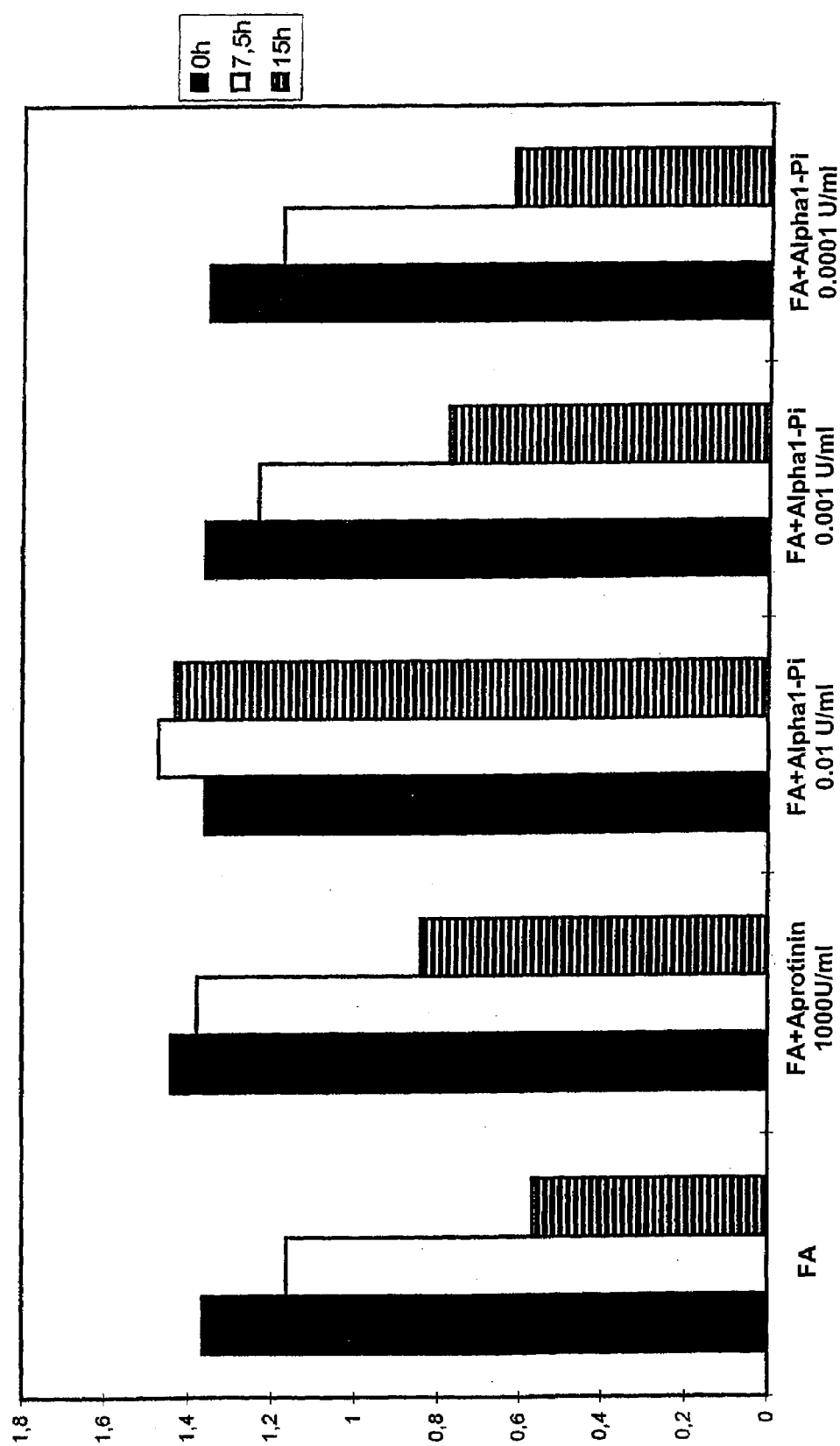
FIG. 1 shows the decrease of-extinction corresponding to an increasing lysis of the clot a) fibrin adhesive without aprotinin
b) fibrin adhesive with aprotinin (1,000 U/ml)
c) fibrin adhesive with alpha-1 PI (0.01 U/ml)
d) fibrin adhesive with alpha-1 PI (0.001 U/ml)
e) fibrin adhesive with alpha-1 PI (0.0001 U/ml)

1. In Vitro-Tests for Assaying the Fibrinolysis-Inhibiting Action of the Tissue Adhesive According to the Invention (at Present Considered by Applicant to be the Best Mode of Carrying out the Invention)

In this Example, blocking of the lysis of a tissue adhesive clot by means of eglin or $\alpha_1$-antiprotease is shown. In this instance, the tissue adhesive STIM3 (IMMUNO AG, Vienna, AT) (comprising 70 mg of fibrinogen/ml) is dissolved in water and subsequently diluted 1:6 with an 0.9 M NaCl solution.

This tissue adhesive solution is mixed 1:1 with a thrombin solution that had been dissolved in 40 mM $CaCl_2$ and subsequently had been diluted with a 40 mM $CaCl_2$/0.9 M NaCl (1:5) solution to 0.1 U/ml, and pipetted on a micro plate, with 100 µl/well being provided.

Various concentrations of the inhibitors were added to each 5 µl of tissue adhesive (Eglin 1-100 µg/ml, $\alpha_1$-antiprotease 0.01-1 U/ml).

Figure 2:
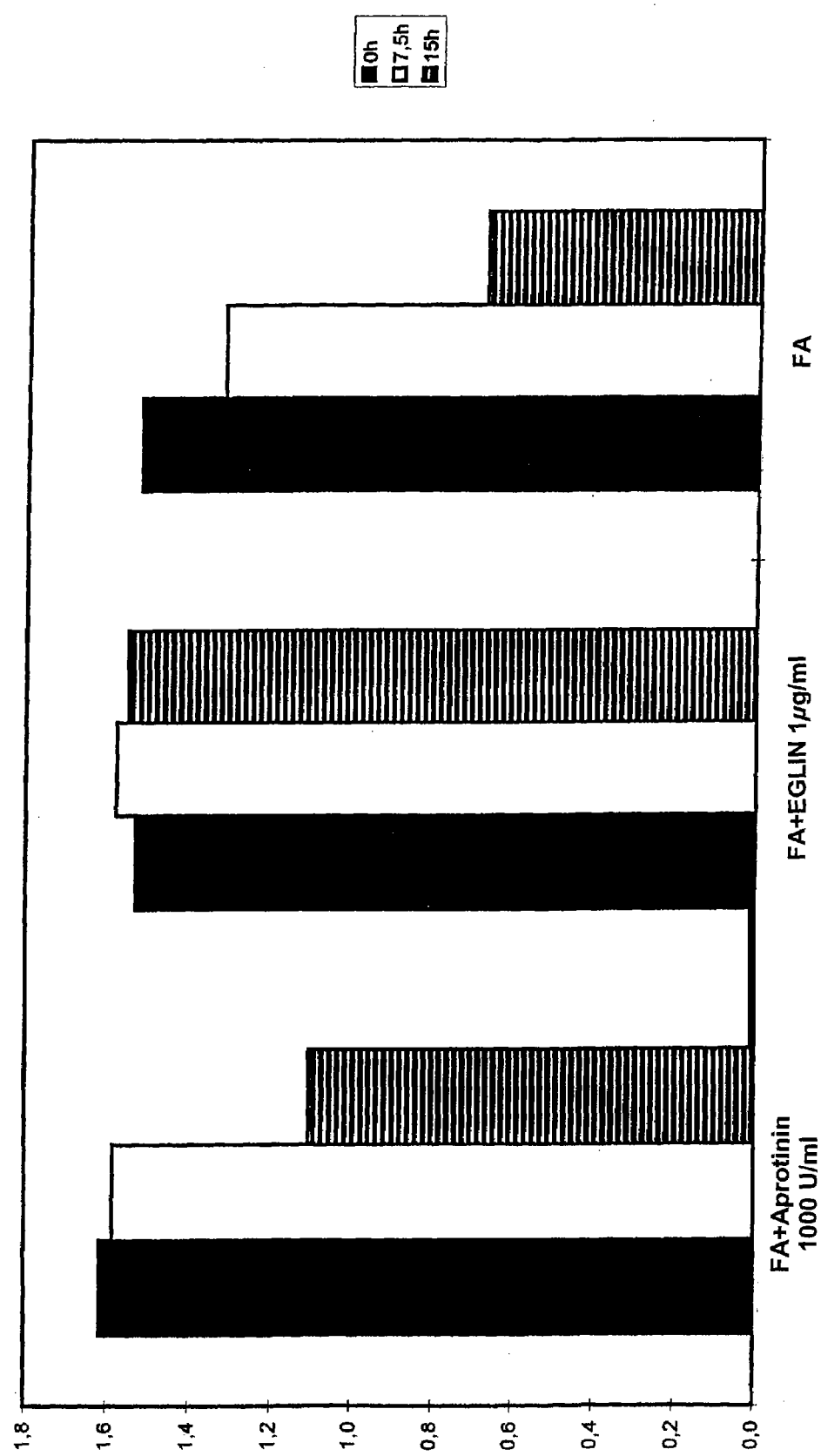
FIG. 2 shows the decrease of extinction corresponding to an increasing lysis of the clot
a) fibrin adhesive with aprotinin (1,000 U/ml)
b) fibrin adhesive with eglin (1 µg/ml)
c) fibrin adhesive without aprotinin.

For hardening of the adhesive, the microtiter plate was incubated at 37° C. for approximately 1.5 hours. The corresponding lysis reagents (a: cell-free supernatant from leukocyte homogenate (3× freezing/thawing) of 500,000 leukocytes/µl; b: t-PA 2 mg/ml as positive control; NaCl 0.9% as negative control) were then pipetted onto the clots (100 µl/well). Subsequently, the microtiter wells were measured in the plate photometer at 37° C. at a wave length of 405 nm kinetically over night 60×900 s in the Photometer SLT 340 ATTC. The results are illustrated in FIGS. 1 and 2, the decrease in the extinction corresponding to the increasing lysis of the clots.

It has been shown that both, with $\geq 1$ µg of eglin/ml and with $\geq 0.01$ U of $\alpha_1$-antiprotease/ml it is possible to prevent the lysis of the fibrin clot which occurs in the assay within 15 hours, which, on the one hand, is a hint to the central role played by the leukocyte proteases for the degradation of the fibrin clot and, on the other hand, shows the excellent effect of the inventive elastase inhibitors for preventing this lysis.

2. In Vivo Activity of the Elastase Inhibitors Used According to the Invention

To determine the importance of leukocyte proteases, in particular elastase inhibitors, within the scope of the present invention, the effect of the tissue adhesive of the invention both in hyper-fibrinolytic systems and in case of normal fibrinolytic activity were tested to illustrate hemostasis by means of tissue adhesive and compared with adhesives without inhibitors, and with an adhesive containing only aprotinin as plasmin inhibitor, respectively.

2.a) Hyperfibrinolysis

Anesthetized rabbits (2-3 kg) were heparinized (4,000 U/kg). Half an hour later, a part of the right liver lobe was clamped and partially resected distal from the clamp. Hemorrhages from larger vessels were stopped by electrocoagulation, and the residual diffuse haemorrhage was sealed by applying tissue adhesive (max. 4 ml) within 200 seconds. 10 minutes later, infusion of t-PA (700 U/kg/h) was started, and the extent of rebleeding was determined for 2 hours by measuring the increase in weight of pre-weighed pads.

In doing so, 3 different tissue adhesives were tested.
a) Tissue adhesive (STIM3) with aprotinin (3,000 U/ml) as negative control
b) Tissue adhesive (STIM3) without aprotinin as positive control
c) Tissue adhesive (STIM3) without aprotinin, with eglin (10 µg/ml); adhesive according to the invention These adhesives were blind-tested and applied by means of a Duploject® syringe (from IMMUNO, Vienna, AT).

Figure 3:
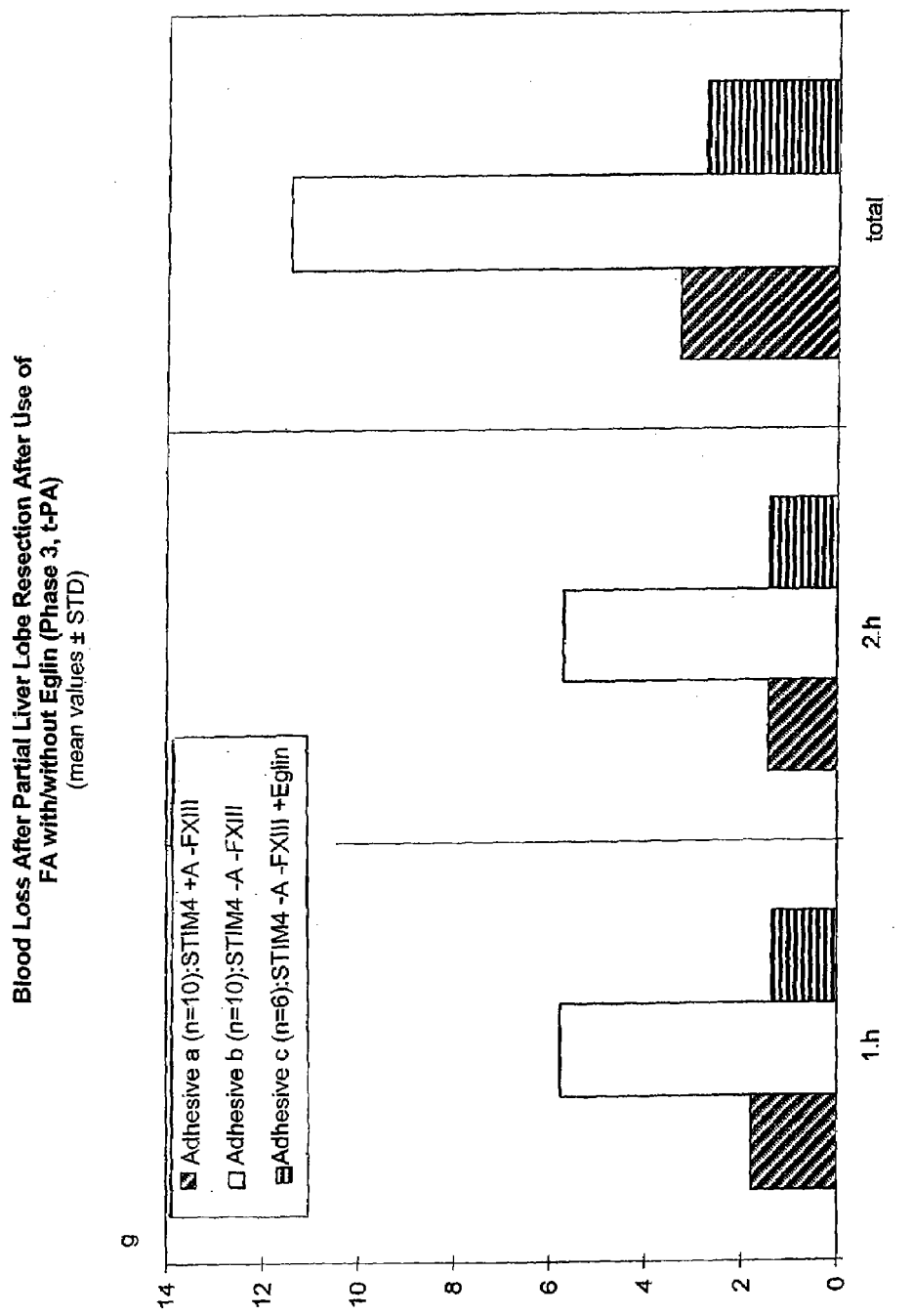
FIG. 3 shows the extent of rebleeding, expressed by the increase in the weight of the pre-weighed pads, in a hyper-fibrinolytic environment, which had been induced by infusion of t-PA.

The results obtained are illustrated in FIG. 3.

2.b) Normal Fibrinolytic Activity

Figure 4:
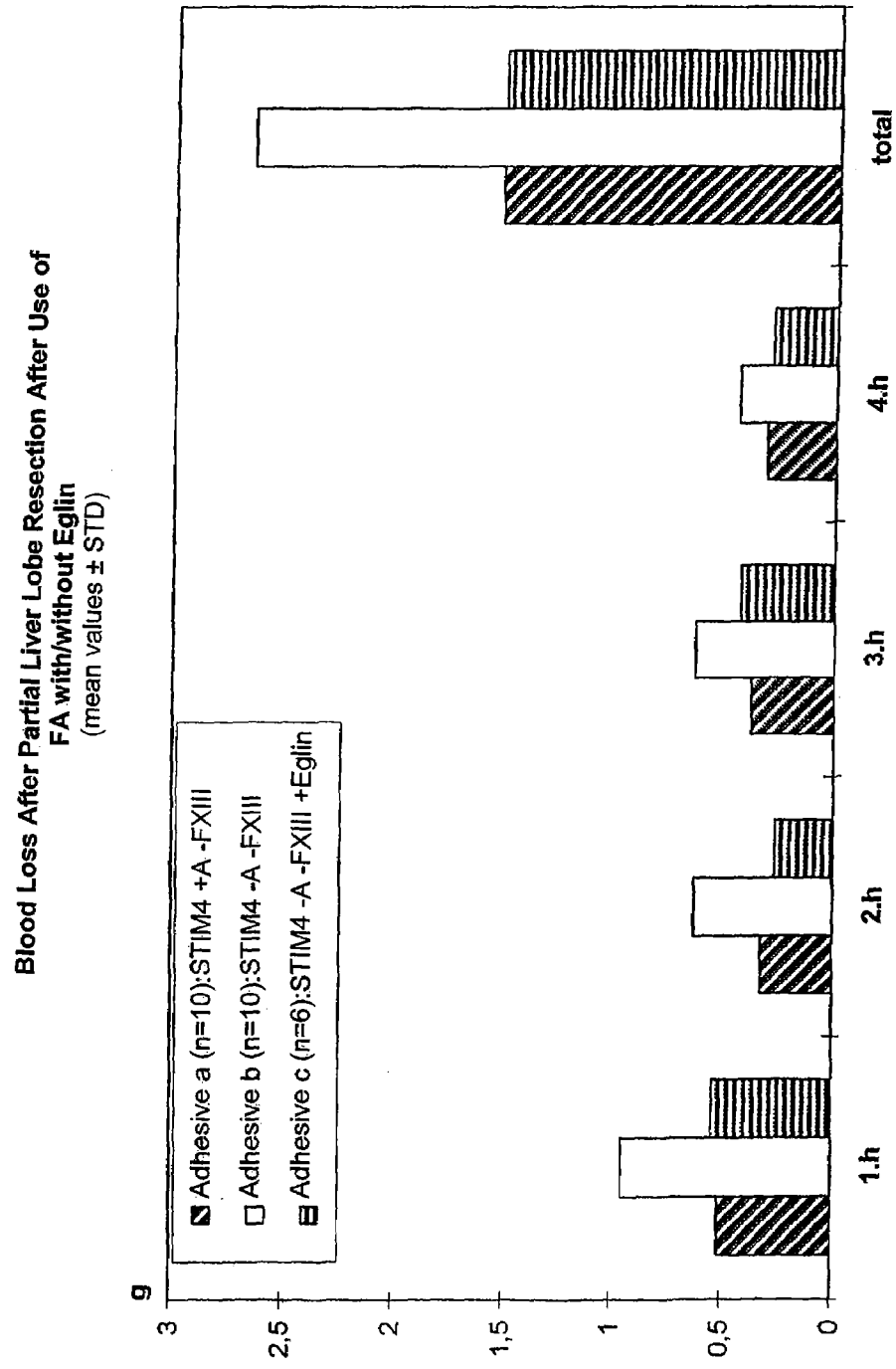
FIG. 4 shows the extent of rebleeding, expressed by the increase in the weight of pre-weighed pads, in an environment with normal fibrinolytic activity, i.e. without t-PA infusion.

In addition to the hyperfibrinolysis-model, also the same assays were carried out without t-PA infusion, yet with increased observation periods of 4 hours. The results obtained are illustrated in FIG. 4.

It has been shown that both, in the hyperfibrinolysis model and with normal fibrinolysis, reduced rebleeding is achieved as compared to conventional adhesives, with improved properties as compared to aprotinin, primarily in case of longer lysis periods.

These results prove the excellent effects of the tissue adhesives according to the invention, with which an early lysis of the fibrin adhesive can be prevented, whereby rebleedings could be prevented also in fields with high fibrinolytic activity.

What is claimed is:

1. A fibrinogen-based tissue adhesive, characterized in that it comprises a therapeutically effective amount of fibrinogen admixed with 0.001-0.0001 U/ml of elastase alpha-1 proteinase inhibitor.

2. A tissue adhesive of claim 1, wherein said tissue adhesive is comprised of human proteins.

3. A tissue adhesive of claim 1, wherein said tissue adhesive is comprised of human blood or plasma proteins characterized in that it is composed exclusively of human blood or plasma proteins.

4. A tissue adhesive of claim 1, wherein ratio in weight of the elastase alpha-1 proteinase inhibitor to said fibrinogen is from 1:500 to 1:110,000.

5. A tissue adhesive of claim 1, wherein said tissue adhesive contains at least $10^{-6}$ U of elastase alpha-1 proteinase inhibitor per gram of fibrinogen.

6. A tissue adhesive of claim 1, further comprising plasminogen in an amount of at least 0.0001 mg/mg of fibrinogen.

7. A tissue adhesive of claim 1, wherein it does not contain any plasminogen.

8. A tissue adhesive of claim 1, wherein it further comprises a plasmin activator inhibitor which is selected from the group consisting of aprotinin, alpha-2-macroglobulin, alpha-1-antitrypsin, e-aminocaproic acid, tranexamic acid, and mixtures thereof.

9. A tissue adhesive of claim 1, wherein it further comprises an antibiotic which is selected from the group consisting of aminoglycosides, betalactams, polypeptides, phosphomycin, tetracyclines and mixtures thereof.

10. A tissue adhesive of claim 1, wherein it comprises Factor XIII in an amount of at least 0.001 U/mg of fibrinogen.

11. A tissue adhesive of claim 1, wherein it is free from kininogenic proteins.

12. A tissue adhesive of claim 1, wherein the tissue adhesive is present in combination with a solid surface as a fleece.

13. A tissue adhesive of claim 12, wherein the solid surface is a collagen, gelatin or polysaccharide surface.

14. A tissue adhesive of claim 1, wherein in an environment of high fibrinolytic activity it is resistant to lysis for a period of time of at least 10 hours.

15. A tissue adhesive of claim 1, wherein it is lyophilized.

16. A tissue adhesive of claim 1, wherein it is present in solution.

17. A tissue adhesive of claim 16, wherein the solution is deep frozen.

18. A tissue adhesive of claim 1, wherein it is present in virus inactivated form.

19. A tissue adhesive of claim 1, wherein the elastase alpha-1 proteinase inhibitor is of recombinant origin.

20. A tissue adhesive system, wherein it comprises the tissue adhesive of claim 1 as one component thereof.

21. A tissue adhesive system of claim 20, wherein it further comprises thrombin and optionally calcium.

22. A tissue adhesive system, comprising a therapeutically effective amount of fibrinogen and 0.001-0.0001 U/ml of elastase alpha-1 proteinase inhibitor.

23. A tissue adhesive system of claim 22, wherein it further comprises an application device for the components of the system, in particular a double-syringe system.

* * * * *

UNITED STATES PATENT AND TRADEMARK OFFICE
CERTIFICATE OF CORRECTION

| | | |
|---|---|---|
| PATENT NO. | : 7,892,802 B2 | Page 1 of 1 |
| APPLICATION NO. | : 12/252988 | |
| DATED | : February 22, 2011 | |
| INVENTOR(S) | : Heinz Redl et al. | |

It is certified that error appears in the above-identified patent and that said Letters Patent is hereby corrected as shown below:

On the Title Page

After Item (63), please insert: Item -- (30)  Foreign Application Priority Data

Aug. 28, 1997  (AT).....................1449/97 --

Signed and Sealed this

Twenty-sixth Day of April, 2011

David J. Kappos
*Director of the United States Patent and Trademark Office*